United States Patent

Cady et al.

[11] 4,072,578
[45] Feb. 7, 1978

[54] MULTI-CHAMBERED MODULE FOR USE IN MONITORING GROWTH OF MICROORGANISMS

[75] Inventors: Paxton Cady; Takeshi Omura; Melvin Rudin, all of Los Altos; James H. Fleming, Palo Alto, all of Calif.

[73] Assignee: Bactomatic Corporation, Palo Alto, Calif.

[21] Appl. No.: 679,385

[22] Filed: Apr. 22, 1976

Related U.S. Application Data

[63] Continuation-in-part of Ser. No. 633,213, Nov. 19, 1975.

[51] Int. Cl.² .............................................. C12K 1/04
[52] U.S. Cl. ............................... 195/127; 204/195 W
[58] Field of Search ................ 195/103.5 R, 127, 139; 204/195 W

[56] References Cited

U.S. PATENT DOCUMENTS

| 3,240,693 | 3/1966 | Gardner | 204/195 W |
| 3,743,581 | 4/1973 | Cady et al. | 195/103.5 R |
| 3,890,201 | 6/1975 | Cady | 195/127 |

Primary Examiner—Raymond N. Jones
Assistant Examiner—Robert J. Warden
Attorney, Agent, or Firm—Phillips, Moore, Weissenberger, Lempio & Majestic

[57] ABSTRACT

A multi-chambered module for holding separate samples of nutrient media. A plurality of chambers, with access means into each, is permanently attached to an electrically non-conductive base. Embedded within the base under the chambers is a plurality of electrically conductive leads. Terminal portions at one end of the leads emerge in spaced pairs into each chamber forming electrodes therein. At the other end of the leads terminal portions are exposed for contact with an electrical source. A signal passed through the electrodes in galvanic contact with media permits the impedance thereof to be determined, with changes of impedance directly associated with microorganism growth therein.

14 Claims, 4 Drawing Figures

MULTI-CHAMBERED MODULE FOR USE IN MONITORING GROWTH OF MICROORGANISMS

This application is a continuation-in-part of application Ser. No. 633,213, filed Nov. 19, 1975.

BACKGROUND OF THE INVENTION

This invention relates to containers which hold media for use in detecting growth of microorganisms therein and more particularly concerns a multi-chambered module coordinated for use in an apparatus which assesses matabolic activity by monitoring the electrical, namely impedance, characteristics of nutrient media containing microorganisms.

A technique recently has been developed whereby growth of various types of microorganisms can be determined by measuring the changes of electrical properties of nutrient media containing the suspected microorganisms. For instance, in U.S. Pat. No. 3,743,581 changes in electrical conductivity of the medium indicate metabolic activity, whereas in U.S. Pat. No. 3,890,201 the growth or increase of microorganisms in a nutrient medium is correlated to the changes of impedance of the medium. Not only is metabolic activity determinable by the electrical characteristic method, but indications of quantity, identification, and antibiotic susceptibility are more rapidly achieved than by the previously known methods.

As the electrical measurement technique, especially in determining impedance changes, becomes more refined and automated, it becomes more critical to have a carrier or container for holding the nutrient media which is compatible with the progressions and advances of the techniques. In U.S. Pat. No. 3,743,581, for example, a basic media containing cell has been disclosed. For individual measurements the singular cell is acceptable, but newer apparatuses employing the impedance measuring technique are capable of monitoring many cells of growth media rapidly and accurately with individual recordings or computer analysis of each. In U.S. Pat. No. 3,890,201, an impedance measuring module has been taught which provides a plurality of individualized chambers for holding many samples of growth media. However, even in this plural-chambered module there are a number of deficiencies and shortcomings which indicate that there is room for further improvement.

To measure impedance changes of nutrient media the container contains at least two electrodes in contact with the media. An electrical signal passed through the electrodes allows the impedance of the media to be determined. The multiple chamber module previously mentioned includes metal conductors for electrodes on the top of a circuit board; with careless handling the exposed metallic strips may be readily damaged. Furthermore, long metallic leads extend to some of the chambers, thereby having segments with large areas of exposure; these long leads are subject to oxidation, fingerprints, scratches and other environmental conditions which may distort and unpredictably vary the reliability of the data being sought. Moreover, the individual chambers of the known plural-chambered module are attached directly over, and are resting on, the leads connected to the electrodes. This attachment scheme may not only damage the leads or interfere with their continuity, but also increases the chances of uneven placement of the chambers. Uneven placement of chambers undesirably increases the opportunity for media to escape and cross-contaminate media in other chambers.

Another shortcoming in the known plural-chambered module is that the individualized nature of the chambers (cylinders) precludes mass production methods. As the apparatuses for correlating microorganism growth with impedance changes of media become more sophisticated, there is a need for sufficient quantities of plural-chambered modules to justify mass production thereof for obvious economic reasons.

SUMMARY OF THE INVENTION

Not only does the multi-chambered module of the present invention overcome the deficiencies of the known modules as discussed above, but it also offers further advantages as well. This new multi-chambered module as defined herein has the electrical leads to each chamber embedded in an electrically non-conductive material, with only the electrode portions in the chambers and the portions for connection to an electrical source exposed. One prominent advantage gained is that there are no unnecessarily exposed leads, which significantly reduces the probability of damage compared to prior modules. Furthermore, another advantage is that the embedded leads are more strongly supported within the base and are not exposed to environmental conditions; this means that variations of readings due to oxidation, fingerprints, etc., of the leads are also effectively diminished.

Further still, by having embedded leads, the chambers for holding media rest naturally flush on the supporting base for an excellent seal with chances for cross-contamination of media virtually eliminated. Along this line, the new module may be formed or molded in one piece so that the individual chambers are integrally and permanently part of the supporting base. This not only increases structural integrity, but very effectively compartmentalizes the chambers to keep the media safely therein.

By fabricating the multi-chambered module of an integrally formed unitary structure, various mass production techniques such as injection molding, casting and the like may be employed to reduce the manufacturing expense, which is indeed an economic advantage. Additionally, as the expense of volume produced modules decreases, the modules may be disposed of after one use which is very desirable from the microbiological standpoint. In fact, it is offered that the injection molded, integrally formed modules of this invention are presently disposable, to be discarded after all the chambers have been used only one time. By using each chamber merely once, cleaning problems, considerations of residue deposits of prior microorganisms, maintenance and other concerns are eliminated.

In accordance with the principles of this invention, a multi-chambered module for use in monitoring growth of microorganisms in specimens of nutrient media includes an electrically non-conductive base. Permanently attached to the base is a plurality of chambers with each chamber having access means for placing a sample or specimen material therein. Embedded within the base under the chambers is a plurality of electrically conductive leads. At one end of the leads the terminal portions thereof emerge in pairs into each chamber in spaced relationship to each other to form electrodes for galvanic contact with the media in the chamber. On the other end of the leads those terminal portions are exposed for contact with an electrical source.

In the preferred embodiment of the multi-chambered module the base is generally flat and rigid. The chambers are integrally attached to the base so that a unitary structure is formed, and the access means is an opening in the top of each chamber. Within the base the leads lie flat and the terminal portions at one end emerge into the chambers in angular disposition, such as right angles, with respect to the plane of the base. This module is most desirably injection molded of plastic material, preferably clear for visual observation of the contents of the chambers. Furthermore, for practical purposes, this embodiment includes the terminal portions of the leads for electrical contact aligned adjacent each other and spaced for mating with an electrical connector.

Variations of the fundamental module of this invention include a cover for the access means in the chambers; also, the module may include nutrient media in one or more chambers as a prepared package.

In the preferred embodiment in which the leads emerge in angular disposition, or upright, as electrodes into the chambers an unexpected advantage over the prior art modules is realized. When growth media, for instance, used to monitor metabolic activity in food samples are tested, quite frequently particles or sediment tend to settle on the bottom of the chambers. In the module disclosed in U.S. Pat. No. 3,890,201, this sediment rests directly on and across the electrodes which lie horizontally on the bottom of the chambers. As a result the impedance measurement at the electrodes tends to relate more closely to metabolic activity on the sedimentary particles, which is significantly different than the average metabolic activity occurring within the media itself. Consequently, the data collected may be somewhat inaccurate, especially when comparing information with growth media having no sedimentary instances.

On the other hand the electrodes in the preferred embodiment of the present invention extend uprightly in the chambers. If sediment bottoms in these chambers it does not completely cover the electrodes; the upright electrodes remain virtually free of sediment, except at the very base of the chamber. In this respect the impedance is measured across the growth media itself, rather than across gravity-induced sediment. Data produced by the preferred module of this invention is, then, more reproducible and, consequently, more reliable.

BRIEF DESCRIPTION OF THE DRAWINGS

These and other advantages, features and aspects of the invention will become apparent upon reading the following detailed description and upon reference to the accompanying drawings, in which.

While the invention will be described in connection with a preferred embodiment, it is understood that it is not intended to limit the invention to that embodiment. On the contrary, it is intended to cover all alternatives, modifications and equivalents as may be included within the spirit and scope of the described invention.

DETAILED DESCRIPTION OF THE DRAWINGS

Figure 1:
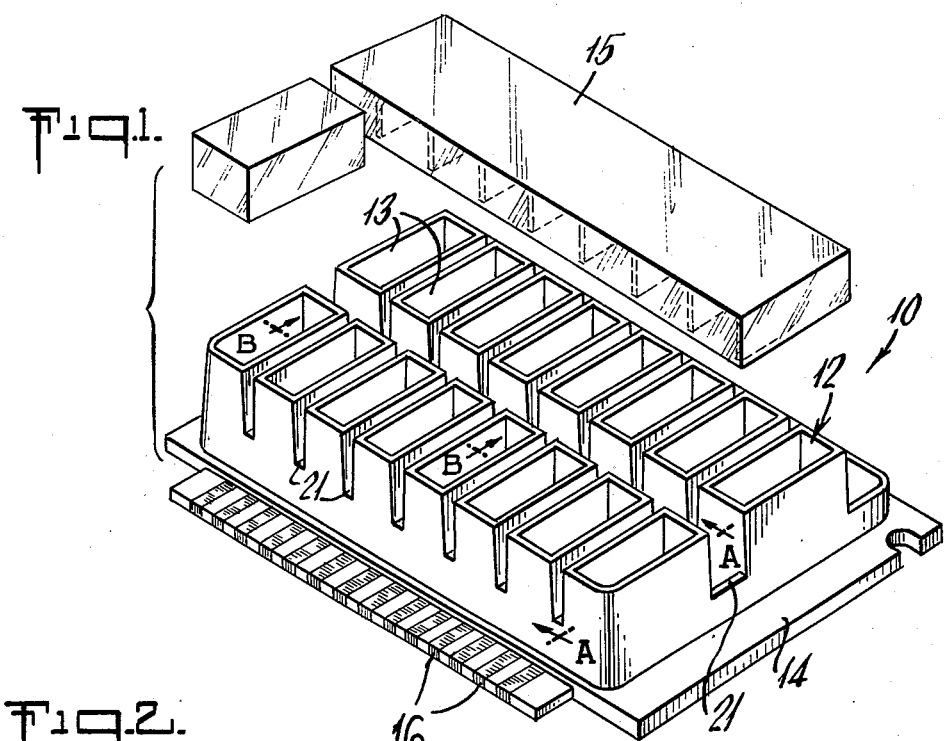
FIG. 1 is a perspective view of the preferred module.

Adverting to the drawings in which a preferred embodiment is illustrated, there is shown in FIG. 1 a multi-chambered module 10 for use in monitoring growth of microorganisms. Included in the module 10 is an electrically non-conductive base 14. Although at times some flexibility or resiliency may be required of the base 14, it is preferably rigid in most instances, and flat in order to act as a support. While there are no thickness or shape restrictions on the base 14, considerations of weight, expense, structural integrity, apparatus with which the module is used, and the like usually control the final dimensions of the base.

A plurality of chambers 12 is attached to the base on one side thereof. These chambers 12 are for holding the specimens of nutrient media in which the microorganisms grow. As seen in the preferred embodiment, the chambers 12 have openings 13 in the top as a means of access for placing samples of nutrient media, suspected contaminants and the like in the chambers. The media is generally a liquid substance which is supportive of microorganism growth and may be homogeneous or non-homogeneous. Various means of access to the interior of the chamber, such as small holes in the upper walls of the chambers, may be employed as long as a sample to be tested for microorganism growth may be placed within the chamber 12.

In order to electrically isolate the contents of each chamber 12 from that of other chambers, it is preferred that the chambers be made of electrically non-conductive material. However, if electrically conductive material is used on the chambers, at least the interior surfaces of each chamber 12 should be electrically non-conductive for the most accurate and reliable results.

Figure 2:
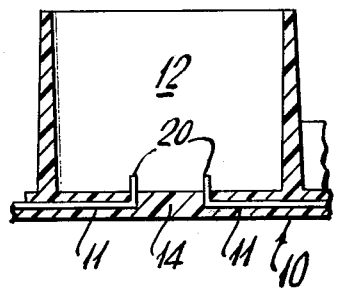
FIG. 2 is a cross-sectional view taken along lines A—A of FIG. 1.
Figure 3:
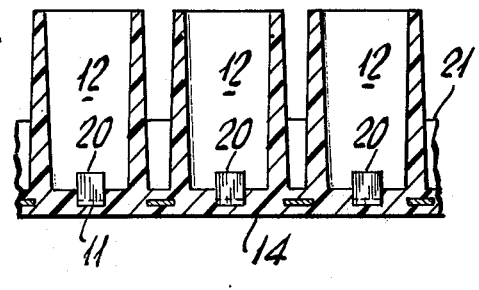
FIG. 3 is a cross-sectional view taken along lines B—B of FIG. 1.

As more clearly seen in FIGS. 2 and 3, embedded within the base 14 and under the chambers 12 is a plurality of electrically conductive leads 11. Terminal portions at one end of the leads 11 emerge in pairs into each chamber 12 in spaced relationship to each other to form electrodes 20. Since the leads 11 generally lie flat within the plane of the base 14 in which they are embedded, the terminal portions thereof are merely turned up in angular disposition so that the electrodes 20 emerge in an upright position into the respective chambers 12. Most conveniently, the electrodes 20 emerge into the chambers 12 at right angles or about 90° with respect to the plane of the base 14. The electrodes 20 contact the growth media placed within the chambers, and when an electrical signal is passed through the electrodes the impedance of the media is determinable due to the galvanic contact established between media and electrodes 20. In the apparatus in which this module 10 is used changes of impedance of the media are directly correlated to growth of microorganisms within. By this electrical determination of metabolic growth the time for detection of harmful amounts or types of microorganisms is tremendously shortened over the slower, known techniques. To be adapted to the impedance measuring apparatus terminal portions 16 on the other end of the leads 11 are exposed for contact with an electrical source.

For instance, terminal portions 16, as seen in FIG. 1, emerge from under the chambers 12 and lie supported on one surface of the base 14. In the most convenient arrangement the terminal portions 16 are aligned adjacent each other and are spaced for mating with an electrical connector of whatever type may be practical.

Although the chambers are individualized, the electrodes 20 may be arranged so that pairs of chambers 12 are electrically connected in series; i.e., one electrode in each chamber of the pair is connected to one electrode in the other chamber of the pair, and the remaining electrode in each chamber is connected to a different contact of the electrical source. By having a pair of chambers 12 series connected it becomes possible to measure the impedance ratio of media contained therein rather than absolute measurements.

To prevent the media within the chambers 12 from escaping or splashing a cover 15 is provided to close the access means or opening 13. The cover 15 may be individualized to protect singular chambers 12, or one cover may protect a plurality, or even all, of the chambers. Furthermore, in instances where excess gas build-up in the chambers needs relief, or where oxygen is required to stimulate growth of the contents, such as with chambers containing aerobic organisms, the cover 15 may be provided with means such as ridges, grooves, side dents and the like, to channel air in or out of the chamber while still protecting the media within from splashing or escaping. Plastic covers are suitably convenient for this invention; however, many different covers are applicable, including various types of adhesive strips, tapes or membranes.

While there are any number of ways to manufacture a module as described above, molding processes, especially injection molding, have been found preferable from a practical and economic viewpoint. Moreover, since the most desirable material for the modules is plastic, the configuration and essential features of the module are readily achieved by the molding techniques. Also, by molding the module the chambers 12 and base 14 are integrally formed into a unitary structure of the same material. This integral structure not only provides strength and rigidity, but compartmentalizes the individual chambers more effectively than by attaching separate chambers to the base. The choice of plastic material for the module is manifold; plastics such as styrene acrylonitrile are very suitable in that they form hard, rigid structures, but are lightweight and transparent to allow visual observation of the media in the chambers. Of course, the configurations of the modules are unlimited; for instance, the module in FIG. 1 has 16 chambers, each of which may hold up to 2 cubic centimeters of media therein. Furthermore, the module configuration may include features for additional strength and support such as walls 21. These walls 21, in essence, half-walls, increase the rigidity, strength and integrity of the module by stiffening the areas between adjacent chambers 12. Additional module strength is helpful during the molding steps and especially during insertion and extraction of the module from the measuring apparatus.

Molding the module also provides a convenient method to embed the leads in the base under the chambers. The molding method allows the leads 11 as seen in FIGS. 2 and 3, to be situated in the base 14 so that the plastic material envelopes and completely insulates the leads while providing strong, solid support therefor. In addition, electrical lead layout regarding positioning and direction to each chamber and the electrical source contact is facilitated, especially in the module molding process of fabrication.

Figure 4:
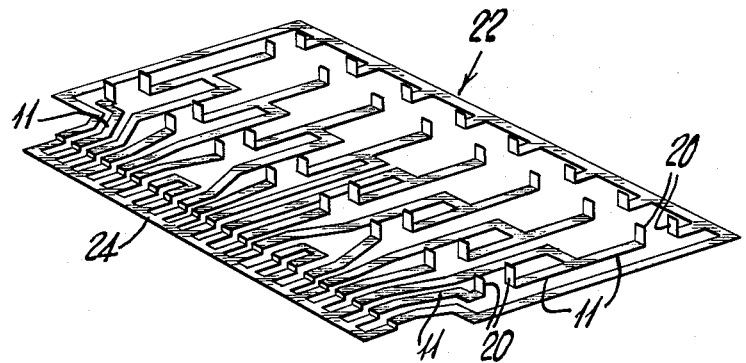
FIG. 4 is a perspective view of the electrical leads in a typical frame configuration before being incorporated into the module.

Specifically, as seen in FIG. 4, the leads 11 are thin strips of metal, punched, stamped or otherwise formed into a frame 22 of the desired configuration. In the embodiment being described the lead frame 22 is stainless steel, between 0.010 and 0.025 inches (0.0254 and 0.0635 cm.) thick, with electrodes 20 standing perpendicular to the leads 11. This frame 22 is handled as a unit, and is inserted in one quick step into the module molding device. Upon completion of the molding steps, edge 24 is cut away so that electrical continuity in the frame 22 is broken and leads 11, now solidly embedded in the base of the module are electrically individualized, or connected in various electrical configurations, as desired. Use of the lead frame approach obviates insertion of individual leads for inclusion in the module, thereby saving considerable fabrication time.

Whereas the module described above does not contain growth media until the operator is ready to perform the test, in some instances the module may contain nutrient media in one or more chambers as a shelf or stock prepared package. In that case, cover means is generally included with the module to keep the media within the chambers. Access means is provided on these modules to allow the operator to place a suspected contaminant or other test sample into the media for the purpose of monitoring ensuing metabolic activity.

Thus, it is apparent that there has been provided in accordance with the invention a multi-chambered module that fully satisfies the aims, advantages and aspects as set forth above. While the invention has been described in conjunction with specific embodiments thereof, it is evident that many alternatives, modifications and variations will be apparent to those skilled in the art in view of the foregoing description. Accordingly, the plenary invention is intended to embrace all such alternatives, modifications and variations as fall within the broadest scope and spirit of the described invention.

What is claimed is:

1. A multi-chambered module for use in monitoring growth of microorganisms in nutrient media comprising: an electrically non-conductive base; a plurality of chambers lying supported on one surface of and permanently attached to said base, each chamber having access means for placing sample material therein; and a plurality of electrically conductive leads completely embedded within said base under said chambers and lying flat within the plane of said base, terminal portions at one end of said leads emerging in pairs into said chamber in spaced relationship to each other to form electrodes for galvanic contact with said sample material placed within each chamber, said terminal portions emerging into said chambers in angular disposition with respect to the plane of said base, and terminal portions at the other ends of said leads exposed for contact with an electrical source.

2. A module as defined in claim 1 wherein said base is generally flat and rigid.

3. A module as defined in claim 1 wherein said access means is an opening in the top of each chamber.

4. A module as defined in claim 1 wherein said base and said chambers are integrally formed into a unitary structure of the same material.

5. A module as defined in claim 4 wherein said integral structure of base and chambers is made of plastic material.

6. A module as defined in claim 1 wherein said angular disposition of said terminal portions is about 90° with respect to the plane of said base.

7. A module as defined in claim 1 wherein said terminal portions of said leads exposed for electrical contact are aligned adjacent each other and spaced for mating with an electrical connector.

8. A module as defined in claim 1 which further includes means to cover said access means.

9. A module as defined in claim 8 wherein one cover means covers a plurality of said access means in said chambers.

10. A module as defined in claim 1 which further includes support walls between adjacent chambers.

11. A module as defined in claim 1 which further includes nutrient medium in at least one chamber thereof.

12. A module as defined in claim 1 which further includes nutrient media in all chambers thereof.

13. A multi-chamber module for use in monitoring growth of microorganisms in nutrient media comprising: a generally flat, rigid electrically non-conductive base; a plurality of chambers permanently and integrally attached to said base, each chamber having access means for placing a sample material therein; and a plurality of electrically conductive leads completely embedded within said base under said chambers and lying flat within the plane of said base, terminal portions at one end of said leads emerging in pairs into each chamber in spaced relationship to each other to form electrodes for galvanic contact with said media placed within each chamber, said terminal portions of said leads emerging into said chambers in angular disposition with respect to the plane of said base, and terminal portions at the other end of said leads exposed for contact with an electrical source.

14. A module as defined in claim 13 wherein said integrally attached base and chambers are made of plastic material.

* * * * *